United States Patent [19]

Nagata et al.

[11] Patent Number: 5,750,779
[45] Date of Patent: May 12, 1998

[54] PREPARATION PROCESS OF ACYL HALIDE OR SULFONYL HALIDE

[75] Inventors: Teruyuki Nagata; Hidetoshi Hayashi; Hideki Mizuta, all of Fukuoka-ken, Japan

[73] Assignee: Mitsui Toatsu Chemicals, Inc., Tokyo, Japan

[21] Appl. No.: 655,929

[22] Filed: May 31, 1996

[30] Foreign Application Priority Data

Jun. 20, 1995 [JP] Japan ................................. 7-152826

[51] Int. Cl.$^6$ .......................... C07C 51/60; C07C 53/42
[52] U.S. Cl. ................ 562/828; 562/832; 562/833; 562/849; 562/852; 562/857; 562/861
[58] Field of Search ..................... 562/828, 831, 562/834, 853, 854, 855, 856, 832, 833, 849, 852, 861, 857

[56] References Cited

U.S. PATENT DOCUMENTS 3,282,924  11/1966  Alt .
5,430,186   7/1995  Ksoll et al. ........................ 562/857

OTHER PUBLICATIONS

Chemical Abstracts, vol. 118, No. 23, Jun. 7, 1993, Columbus, OH, US; Abstract No. 233463y; T. Isobe et al; Halogenation of Primary Alcohols, p. 949, XP002014957 *abstract* & JP-A-04308538 (Shiratori Pharmaceutical Co., Ltd.) Oct. 30, 1992.

Kirk-Othmer, "Encyclopedia of Chemical Technology", 3rd Ed., vol. 17, 1982, John Wiley & Sons, New York, XP002015405, pp. 416–425.

Chemical Abstracts, vol. 118, No. 23, Jun. 7, 1993, Columbus, OH, US; Abstract No. 233484f, T. Isobe et al; "Manufacture of 3-Halo-2,3-unsaturated-ketones", p. 943, XP002014960 *abstract* & JP-A-04308547 (Shiratori Pharmaceutical Co., Ltd.) Oct. 30, 1992.

Chemical Abstracts, vol. 101, No. 15, Oct. 8, 1984, Columbus, OH, US; Abstract No. 130410y; Shiratoriseyaku: "Esterification of Alcohols and Carboxylic Acids", p. 683; XP002015385 *abstract* & JP-A-59039851 (Shiratori Pharmaceutical Co., Ltd.), Aug. 26, 1982.

Chemcial Abstracts, vol. 101, No. 17, Oct. 22, 1984, Columbus, OH, US; Abstract No. 151844h, Shiratori Seyyaku, "1,3-Dimethyl-2-Cloroimidazolium Chloride", p. 716; XP002015386 *abstract* &JP-A59025375 (Shiratori Pharmaceutical Co., Ltd.) Feb. 9, 1984).

Chem.Ber., vol. 112, 1979, Weinheim, pp. 1670–1679, XP002014419, W. Seufert et al: "Zur Halogenierung Von Enaminen-Darstellung Von Beta-Halogeniminium-Halogeniden".

Morrison et al., Organic Chemistry, Fourth Edition, pp. 485–486, 519, 797–801, 1983.

Primary Examiner—Mukund J. Shah
Assistant Examiner—Deepak R. Rao
Attorney, Agent, or Firm—Burns, Doane, Swecker & Mathis

[57] ABSTRACT

A preparation process of acyl halide or sulfonyl halide which comprises reacting corresponding carboxylic acid or sulfonic acid with a haloiminium salt represented by the general formula (1):

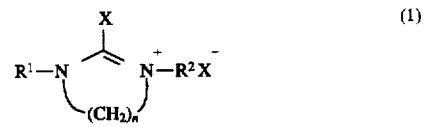

wherein $R^1$ and $R^2$ are same or different lower alkyl groups, X is a halogen atom, and n is an integer of 2 or 3.

20 Claims, No Drawings

PREPARATION PROCESS OF ACYL HALIDE OR SULFONYL HALIDE

BACKGROUND OF THE INVENTION

1. Field of the Invention

The present invention relates to a preparation process of acyl halide or sulfonyl halide.

2. Description of the Related Art

In recent years, acyl halide has become important in industry as an intermediate for preparing heat resistant resins, medicines and agricultural chemicals. For example, lauroyl chloride is used in industry as an intermediate in the preparation of peroxides and surface active agents. Further, terephthaloyl chloride is used for preparing polyesters in industry.

5-Amino-2,4,6-triiodoisophthaloyl dihalide which is obtained by halogenating the acid portion of 5-amino-2,4,6-triiodoisophthalic acid (hereinafter referred to simply as TIPA) is an important compound as a raw material of X-ray contrast medium.

Sulfonyl halide has also become important in industry as an intermediate for preparing medicines and agricultural chemicals.

Acyl chloride is generally prepared by chlorinating carboxylic acid with a chlorinating agent such as thionyl chloride, phosphorus pentachloride, phosphorus trichloride, phosphoryl chloride and phosgene. However, thionyl chloride, phosphorus pentachloride, phosphorus trichloride and phosphoryl chloride are expensive, and have problems on the treatment of sulfur oxides, phosphate compounds and other by-products which are formed by the reaction. Thus, production in an industrial scale accompanies various disadvantages and difficulties in view of economy and environmental protection. Further, phosgene has a lower reactivity than the above chlorinating agents and requires use of a catalyst. Exemplary catalysts which can be used include dimethylformamide, quaternary ammonium salt and sulfonium salt. Dimethylformamide and other lower aliphatic amides are generally used as inexpensive catalysts having high activity.

However, even though these catalysts are used, an active species which is formed from phosgene and dimethylformamide and the other lower aliphatic amides is labile at high temperatures and leads to a problem of drastically increasing the formation velocity of tarry materials at temperatures higher than 100° C.

Further, sulfonyl chloride is generally prepared, for example, by chlorinating sulfonic acid with a chlorinating agent such as thionyl chloride and phosphorus pentachloride. For example, methanesulfonyl chloride is prepared from methanesulfonic acid and thionyl chloride. However, thionyl chloride, phosphorus pentachloride and other chlorinating agents are expensive, and have problems on the treatment of sulfur oxides, phosphate compounds and other by-products which are formed by the reaction. Thus, production in an industrial scale is accompanied by various disadvantages and difficulties in view of economy and environmental protection. Chlorosulfonic acid is frequently used for preparing sulfonyl chloride in industry. For example, p-toluenesulfonyl chloride is prepared in industry from toluene and chlorosulfonic acid and benzenesulfonyl chloride is prepared in industry from benzene and chlorosulfonic acid. However, chlorosulfonic acid causes a violent decomposition reaction with water and forms hydrochloric acid and sulfuric acid. Consequently, handling of chlorosulfonic acid accompanies considerable disadvantages and difficulties as a result of severe corrosivity and strong toxicity.

2-Chloro-1,3-dimethylimidazolinium chloride has been known as a halogenating agent of a primary hydroxyl group in Japanese Laid Open Patent Hei 4-308538. However, the example of utilizing the compounds for preparation of acyl halide or sulfonyl halide has not yet been known.

SUMMARY OF THE INVENTION

The present invention has been carried out in order to overcome the problems on the conventional preparation process of acyl halide or sulfonyl halide. The first object of the invention is to provide an excellent preparation process in economy. The second object of the invention is to provide an excellent process in view of environmental protection.

As a result of an intensive investigation in order to achieve these objects, the present inventors have completed the invention having the following constitution.

That is, various aspects of the invention involve, 1) a preparation process of corresponding acyl halide or sulfonyl halide comprising reacting carboxylic acid or sulfonic acid with a haloiminium salt represented by the general formula (1):

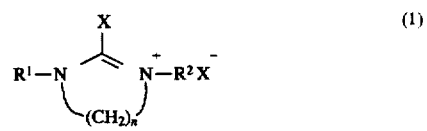

wherein $R^1$ and $R^2$ are same or different lower alkyl groups, X is a halogen atom, and n is an integer of 2 or 3, and 2) a preparation process of corresponding acyl chloride or sulfonyl chloride comprising blowing phosgene into carboxylic acid or sulfonic acid in the presence of a cyclic urea compound represented by the general formula (2):

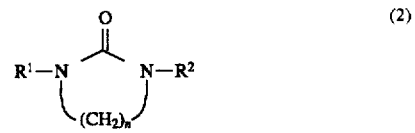

wherein $R^1$ and $R^2$ are same or different lower alkyl groups, and n is an integer of 2 or 3, forming a chloroiminium salt represented by the general formula (3):

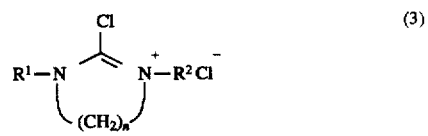

wherein $R^1$ and $R^2$ and n are the same as above, and reacting said carboxylic acid or said sulfonic acid with the chloroiminium salt.

DETAILED DESCRIPTION OF PREFERRED EMBODIMENTS

The haloiminium salt which can be used in the invention is represented by the general formula (1). Exemplary lower alkyl groups represented by $R^1$ and $R^2$ in the general formula (1) include lower alkyl groups having 1–4 carbon atoms such as a methyl, ethyl, n-propyl, isopropyl, n-butyl and isobutyl group. Exemplary halogen atoms represented by X include a fluorine, chlorine, bromine and iodine atom. The chlorine atom is preferred in particular. Preferred examples of the haloiminium salt represented by the general formula (1) include 2-chloro-1,3-dimethylimidazolinium chloride (hereinafter referred to simply as DMC), 2-chloro-1,3-diisopropylimidazolinium chloride, and 2-chloro-1,3-dimethyl-3,4,5,6-tetrahydropyrimidinium chloride.

The haloiminium salt can be obtained with ease by reacting a cyclic urea compound which is known as a readily available solvent and is represented by the formula (2):

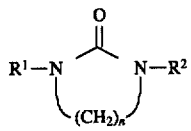
(2)

wherein $R^1$ and $R^2$ and n are the same as above, with a known halogenating agent such as oxalyl halide, phosphorus trihalide, phosphorus pentahalide, phosphorus oxyhalide, phosgene and trichloromethyl chloroformate. Phosgene is now in mass production in the polyurethane industry, inexpensive, and free from generation of industrial wastes such as phosphorus compounds, and thus is most preferred.

The reaction is carried out by dissolving either the compound of the general formula (2) or the halogenating agent in a suitable solvent such as carbon tetrachloride, adding the other reagent by portions to the solution obtained, and reacting for several to dozens of hours at room temperature to 70° C. The haloiminium salt of the general formula (1) thus obtained can be used after isolation. However, the reaction mixture can also be used as intact for the reaction of the invention without isolating the haloiminium salt.

In the first place, the method for reacting the haloiminium salt with carboxylic acids will be illustrated.

The amount of the haloiminium salt is stoichiometric or more, preferably 1.0–2.0 times by equivalent, more preferably 1.1–1.3 times by equivalent for the carboxylic acid.

After finishing the reaction, the haloiminium salt returns to the compound represented by the formula (2), and the compound can be converted again into the haloiminium salt by reacting with the halogenating agent.

The invention includes embodiments for reacting formed iminium chloride with carboxylic acid while preparing iminium chloride wherein X is chlorine atom in the general formula (1). That is, the desired acid chloride can be obtained by charging phosgene into a solution containing the carboxylic acid raw material and the cyclic urea compound of the general formula (2). In the reaction, the cyclic urea of the general formula (2) reacts at first with phosgene to form iminium chloride wherein X is chlorine atom in the general formula (1), and successively carboxylic acid is halogenated by iminium chloride to form the desired carbonyl chloride. In this step, iminium chloride wherein X is chlorine atom in the general formula (1) returns to the cyclic urea of the general formula (2).

Consequently, the amount of cyclic urea of the general formula (2) for use in the reaction is preferably 0.01 equivalent or more, more preferably 0.05–0.1 equivalent for an equivalent of carboxylic acid. Use of cyclic urea in greater amounts does not increase reaction velocity.

The amount of phosgene used in the reaction is 1.0–2.0 equivalents, preferably 1.1–1.3 equivalents for an equivalent of carboxylic acid. The amount is charged over 6–10 hours, preferably over 7–8 hours.

Representative carboxylic acids which can be used in the invention include, for example, formic acid, acetic acid, propionic acid, butanoic acid, isobutanoic acid, pentanoic acid, 3-methylbutanoic acid, pivalic acid, hexanoic acid, heptanoic acid, octanoic acid, nonanoic acid, decanoic acid, myristic acid, palmitic acid, stearic acid, phenylacetic acid, diphenylacetic acid, acetoacetic acid, phenylpropionic acid, cinnamic acid, monochloroacetic acid, dichloroacetic acid, trichloroacetic acid, chloropropionic acid, α-bromoacetic acid, dibromoacetic acid, α-bromopropionic acid and other aliphatic monocarboxylic acids; oxalic acid, malonic acid, succinic acid, methylsuccinic acid, glutaric acid, adipic acid, 1,1-dimethyl-1,3-dicarboxypropane, 1,5-pentanedicarboxylic acid, 1,6-hexanedicarboxylic acid, 1,7-heptanedicarboxylic acid, 1,8-octanedicarboxylic acid, and other aliphatic dicarboxylic acids; benzoic acid, toluic acid, 4-isopropylbenzoic acid, 4-tert-butylbenzoic acid, methoxybenzoic acid, dimethyoxybenzoic acid, 3,4,5-trimethoxybenzoic acid, o-chlorobenzoic acid, 2,6-dichlorobenzoic acid, 3,4-dichlorobenzoic acid, 2,3,6-trichlorobenzoic acid, 4-bromobenzoic acid, and other aromatic monocarboxylic acids; phthalic acid, isophthalic acid, terephthalic acid, 2-chloroterephthalic acid, 2,5-dibromo-terephthalic acid, and other aromatic dicarboxylic acids; lactic acid, butyric acid, 3-hydroxy-2,2-dimethylpropionic acid and other aliphatic carboxylic acids having a secondary hydroxyl group in the molecule; salicylic acid, 5-methoxysalicylic acid, 2-oxy-m-toluic acid, 3,5-di-tert-butylsalicylic acid, p-hydroxybenzoic acid and other aromatic carboxylic acids having a hydroxyl group in a molecule; β-alanine and other aliphatic carboxylic acids having an amino group in the molecule; 4-aminobenzoic acid, 3-aminobenzoic acid, N-methylaminobenzoic acid, m-dimethylaminobenzoic acid, 5-amino-2,4,6-triiodoisophthalic acid and other aromatic carboxylic acids having an amino group in a molecule; and 3-mercaptopropionic acid, o-mercaptobenzoic acid, and other carboxylic acids having a mercapto group in a molecule. However, carboxylic acids are not limited to these compounds. Carboxylic acids having an amino group in a molecule are preferably reacted by using hydrochloride.

It is quite surprising that the above carboxylic acids having an hydroxyl group or amino group in a molecule can be efficiently halogenated by the haloiminium salt of the general formula (1). For example, when the chlorination reaction of carboxylic acids by phosgene in the presence of a known dimethylformamide catalyst is used for the chlorination of aromatic carboxylic acid having an amino group in a molecule, a formamidine derivative is formed and the desired carbonyl chloride cannot be obtained. On the other hand, according to the present invention, the desired carbonyl halide can be prepared from aromatic carboxylic acid having an amino group in a molecule even though the amino group is not protected.

Solvents which can be used for the invention are not restricted in particular so long as the solvents do not react with haloiminium salt of the general formula (1) and are known solvents used for the preparation of acyl halides. Exemplary solvents include, for example, benzene, toluene, xylene, hexane, heptane, cyclohexane and other hydrocarbons; 1,2-dichloroethane, chloroform, carbon tetrachloride, chlorobenzene, dichlorobenzene and other halogenated hydrocarbons; and ethyl acetate, butyl acetate and other esters. However, no restriction is imposed upon these solvents.

The reaction temperature of the invention depends upon the reaction substrate and solvent and is generally in the range of room temperature to 120° C. For example, 75°–80° C. is preferred in the case of 1,2-dichloroethane and 105°–110° C. is preferred in the case of toluene. However, no limitation is put upon these temperatures.

Further, the reaction can also be carried out in the presence of a base. Such method enables acceleration of reaction velocity and reduction of reaction temperature. The bases which can be used include pyridine, triethylamine, and tributylamine.

Acyl halide formed can be isolated from the reaction mixture by common post-treatment methods such as distillation and crystallization.

The reaction of TIPA with haloiminium salt can also be carried out by the above method. Preferred embodiments of the reaction are described below.

The amount of haloiminium salt is stoichiometric or more, preferably 2.0–4.0 times by mole, more preferably 2.1–2.5 times by mole for the amount of TIPA. After finishing the reaction, haloiminium salt returns to the compound of the above general formula (2) and can be converted again to haloiminium salt by reacting with a halogenating agent.

The reaction temperature of TIPA with haloiminium salt preferably 50° C. or more, most preferably 90°–110° C.

Isolation of 5-amino-2,4,6-triiodoisophthaloyl dihalide from the reaction mass obtained can be carried out by removing the solvent from the reaction mass, adding hexane to the residue, and crystallizing 5-amino-2,4,6-triiodoisophthaloyl dihalide.

Next, the method for reacting sulfonic acid with haloiminium salt will be illustrated.

The amount of haloiminium salt is stoichiometric or more, preferably 1.0–1.5 times by equivalent, more preferably 1.1–1.3 times by equivalent for the amount of sulfonic acid.

After finishing the reaction, haloiminium salt returns to the compound of the formula (2) and can be converted again to haloiminium salt by reacting with a halogenating agent.

Sulfonic acids which can be used for the invention include, for example, methanesulfonic acid, benzene sulfonic acid, p-toluenesulfonic acid, 2,5-dimethylbenzenesulfonic acid, 3,4-dimethylbenzenesulfonic acid, m-xylenesulfonic acid, o-dichlorobenzene-4-sulfonic acid, 2,6-dichlorotoluene-4-sulfonic acid, and benzene-1,3-disulfonic acid. However, no restriction is imposed upon these sulfonic acids.

Solvents which can be used for the invention are not restricted in particular so long as the solvents do not react with haloiminium salt of the general formula (1) and are known solvents used for the preparation of acyl halides.

Representative solvents include, for example, benzene, toluene, xylene, hexane, heptane, cyclohexane and other hydrocarbon solvents; 1,2-dichloroethane, chloroform, carbon tetrachloride, chlorobenzene, dichlorobenzene and other halogenated hydrocarbon solvents; and ethyl acetate, butyl acetate and other ester solvents. However, no limitation is imposed upon these solvents.

The reaction temperature in the embodiments of the invention depends upon the reaction substrate and solvent and is generally in the range of room temperature to 120° C. For example, when toluene is used for the solvent, the temperature range is preferably 105°–110° C.

Sulfonyl halide thus formed can be isolated from the reaction mixture by common post-treatment methods such as distillation and crystallization.

When acyl halide or sulfonyl halide is prepared by the invention, the desired product can be efficiently obtained by using haloiminium salt of the general formula (1) in view of economy and environmental protection as compared with conventional methods. The cyclic urea compound of the general formula (2) which is formed by reaction of haloiminium salt of the general formula (1) with carboxylic acid or sulfonic acid, can be recovered and used again for preparing haloiminium salt of the general formula (1). Consequently, the method of the invention has a great advantage in view of economy.

EXAMPLE

The invention will hereinafter be illustrated further in detail by way of examples. However, these examples do not limit the scope of the invention.

Example 1

Synthesis of Lauroyl Chloride

To 9.30 g (0.055 mole) of 2-chloro-1,3-dimethylimidazolinium chloride, 50.1 g of toluene was added and successively 10.02 g (0.05 mole) of lauric acid was added. The mixture was reacted at 110° C. for 4 hours. The reaction mass was analyzed by gas chromatography and liquid chromatography. The conversion ratio of lauric acid was 100% and the yield of lauroyl chloride was 100%.

Example 2

Synthesis of benzoyl chloride

To 9.30 g (0.055 mole) of 2-chloro-1,3-dimethylimidazolinium chloride, 50.1 g of toluene was added, and successively 6.11 g (0.05 mole) of benzoic acid was added. The mixture was reacted at 110° C. for 7 hours. The reaction mass was analyzed by gas chromatography and liquid chromatography. The conversion ratio of benzoic acid was 100% and the yield of benzoyl chloride was 100%.

Example 3

Synthesis of benzoyl chloride

To 9.72 g (0.0575 mole) of 2-chloro-1,3-dimethylimidazolinium chloride, 90 ml of 1,2-dichloroethane and 6.11 g (0.05 mole) of benzoic acid were added. To the mixture obtained, 5.06 g (0.05 mole) of triethylamine was dropwise added over 30 minutes while maintaining the temperature of the mixture at 15°–20° C., and successively reacted at room temperature for 4 hours. The reaction mixture was analyzed by gas chromatography. The yield of benzoyl chloride was 93%.

Example 4

Synthesis of benzoyl chloride

To a four necked flask equipped with a stirrer, gas inlet tube, thermometer and Dimroth condenser, 3.42 g (0.03 mole) of 1,3-dimethylimidazolidine-2-one as a catalyst, 36.64 (0.3 mole) of benzoic acid, and 146.56 g of toluene were charged. Phosgene was blown into the mixture with stirring at a rate of 4.2 g/hour, and the reaction was carried out at 110° C. for 7 hours. The reaction mass was analyzed by gas chromatography. The yield of benzoyl chloride was 95%.

Example 5

Synthesis of terephthaloyl chloride

To 18.6 g (0.11 mole) of 2-chloro-1,3-dimethylimidazolinium chloride, 83 g of toluene was added, and successively 8.31 g (0.05 mole) of terephthalic acid was added. The mixture was reacted at 110° C. for 4 hours. The reaction mass was analyzed by gas chromatography. The yield of terephthaloyl chloride was 98%.

Example 6

Synthesis of succinyl dichloride

To 19.44 g (0.115 mole) of 2-chloro-1,3-dimethylimidazolinium chloride, 83 g of toluene was added and successively 5.90 g (0.05 mole) of succinic acid was added. The mixture was reacted at 110° C. for 11 hours. The reaction mass was analyzed by gas chromatography. The yield of succinyl dichloride as 90%.

Example 7

Synthesis of 5-amino-2,4,6-triodoisophthaloyl dichloride

To a reaction flask, 4.23 g (0.025 mole) of 2-chloro-1,3-dimethylimidazolinium chloride, 5.58 g (0.01 mole) of 5-amino-2,4,6-triiodoisophthalic acid and 80 g of toluene were charged and reacted at 105°–110° C. for 4 hours. Thereafter, the reaction mass was cooled and toluene was removed under reduced pressure. To the concentrate thus obtained, 100 ml of hexane was added to crystallize 5-amino-2,4,6-triiodoisophthaloyl dichloride. The precipitate was filtered and dried under reduced pressure to obtain 5.65 g (95% yield) of 5-amino-2,4,6-triiodoisophthaloyl dichloride as white crystals.

Example 8

Synthesis of 5-amino-2,4,6-triodoisophthaloyl dichloride

The same procedures as described in Example 7 were carried out except that the reaction of 5-amino-2,4,6-triiodoisophthalic acid and 2-chloro-1,3-dimethylimidazolinium chloride was carried out at 90°–95° C. for 6 hours. 5-Amino-2,4,6-triiodoisophthaloyl dichloride thus obtained was 5.53 g (93% yield).

Example 9

Synthesis of hydroxybenzoyl chloride

To 9.72 g (0.0575 mole) of 2-chloro-1,3-dimethylimidazolinium chloride, 90 ml of 1,2-dichloroethane and 6.91 g (0.05 mole) of 4-hydroxybenzoic acid were added. To the mixture, 5.06 g (0.05 mole) of triethylamine was dropwise added over 30 minutes while maintaining the temperature of the mixture at 15°–20° C. Thereafter, the reaction was carried out at 15°–20° C. for 24 hours. The reaction mass was analyzed by gas chromatography and liquid chromatography. Unreacted 4-hydroxybenzoic acid remained 1.79 g (0.013 mole). 4-Hydroxybenzoyl chloride was obtained in the yield of 72%.

Example 10

Synthesis of p-toluenesulfonyl chloride

To 9.72 g (0.0575 mole) of 2-chloro-1,3-dimethylimidazolinium chloride, 83 g of toluene was added and successively 8.61 g (0.05 mole) of p-toluenesulfonic acid was added. The mixture was reacted at 110° C. for 4 hours. The reaction mass was analyzed by gas chromatography. p-Toluenesulfonyl chloride was obtained in the yield of 93.2%.

Example 11

Synthesis of lauroyl chloride

To 93 g (0.55 mole) of 2-chloro-1,3-dimethylimidazolinium chloride, 500 g of toluene and 100.2 g (0.5 mole) of lauric acid were added. The mixture was reacted at 110° C. for 4 hours. The reaction mass was analyzed by gas chromatography and liquid chromatography. The conversion ratio of lauric acid was 100%, and the yield of lauroyl chloride was 100%.

Toluene was distilled from the reaction mass under reduced pressure and successively 56.5 g (0.495 mole) of 1,3-dimethylimidazolidine-2-one was recovered by distillation at 106°–108° C. under reduced pressure of 17 mmHg. Successively, 102.8 g (0.47 mole) of lauroyl chloride was obtained at 142°–144° C. under reduced pressure of 15 mmHg. The yield was 94%.

Comparative Example 1

To a reaction flask, 11.3 g (0.02 mole) of TIPA, 0.15 g (0.002 mole) of dimethylformamide, and 100 ml of toluene were charged and warmed to 70° C. Phosgene was blown into the mixture at a rate of 4 g/hour for 2 hours while maintaining the temperature of the mixture at 70°–80° C. Thereafter, the reaction mass was purged with nitrogen gas at 70°–80° C. for about an hour. After cooling, the reaction mass was filtered and dried under reduced pressure to obtain 9.53 g of crystal. The crystal was a mixture of unreacted TIPA and 2,4,6-triiodo-5-(N,N-dimethylaminomethylidene) aminoisophthaloyl dichloride.

What is claimed is:

1. A preparation process of acyl halide or sulfonyl halide which comprises reacting corresponding carboxylic acid or sulfonic acid with a haloiminium salt represented by the general formula (1):

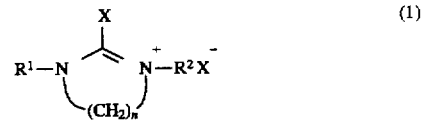

wherein $R^1$ and $R^2$ are same or different lower alkyl groups, X is a halogen atom, and n is an integer of 2 or 3.

2. The preparation process according to claim 1 wherein the carboxylic acid is a compound having a hydroxyl group and/or an amino group.

3. The preparation process according to claim 2 wherein the compound having a hydroxyl group and/or an amino group is an aromatic carboxylic acid having a hydroxyl group.

4. The preparation process according to claim 2 wherein the compound having a hydroxyl group and/or an amino group is an aromatic carboxylic acid having an amino group.

5. The preparation process according to claim 4 wherein the aromatic carboxylic acid having an amino group is 5-amino-2,4,6-triiodoisophthalic acid.

6. The preparation process according to claim 1 wherein the haloiminium salt is 2-chloro-1,3-dimethylimidazolinium chloride.

7. The preparation process according to claim 6 wherein the carboxylic acid is a compound having a hydroxyl group and/or an amino group.

8. The preparation process according to claim 7 wherein the compound having a hydroxyl group and/or an amino group is an aromatic carboxylic acid having a hydroxyl group.

9. The preparation process according to claim 7 wherein the compound having a hydroxyl group and/or an amino group is an aromatic carboxylic acid having an amino group.

10. The preparation process according to claim 9 wherein the aromatic carboxylic acid having an amino group is 5-amino-2,4,6-triiodoisophthalic acid.

11. A preparation process of acyl chloride or sulfonyl chloride which comprises blowing phosgene into corresponding carboxylic acid or sulfonic acid in the presence of a cyclic urea compound represented by the general formula (2):

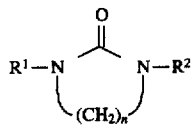

where $R^1$ and $R^2$ are same or different lower alkyl groups, and n is a integer of 2 or 3, forming a chloroiminium salt represented by the general formula (3):

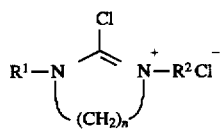

wherein $R^1$, $R^2$ and n are the same as above, and reacting said carboxylic acid or said sulfonic acid with the chloroiminium salt.

12. The preparation process according to claim 11 wherein the carboxylic acid is a compound having a hydroxyl group and/or an amino group.

13. The preparation process according to claim 12 wherein the compound having a hydroxyl group and/or an amino group is an aromatic carboxylic acid having a hydroxyl group.

14. The preparation process according to claim 12 wherein the compound having a hydroxyl group and/or an amino group is an aromatic carboxylic acid having an amino group.

15. The preparation process according to claim 14 wherein the aromatic carboxylic acid having a amino group is 5-amino-2,4,6-triiodoisophthalic acid.

16. The preparation process according to claim 11 wherein the cyclic urea compound is 1,3-dimethylimidazolidine-2-one.

17. The preparation process according to claim 16 wherein the carboxylic acid is a compound having a hydroxyl group and/or an amino group.

18. The preparation process according to claim 17 wherein the compound having a hydroxyl group and/or an amino group is an aromatic carboxylic acid having a hydroxyl group.

19. The preparation process according to claim 17 wherein the compound having a hydroxyl group and/or an amino group is an aromatic carboxylic acid having an amino group.

20. The preparation process according to claim 19 wherein the aromatic carboxylic acid having an amino group is 5-amino-2,4,6-triiodoisophthalic acid.

* * * * *